US012807566B2

(12) United States Patent
Vorholt et al.

(10) Patent No.: US 12,807,566 B2
(45) Date of Patent: Nov. 24, 2026

(54) CATALYTIC SYNTHESIS OF FREE ISOCYANATES

(71) Applicant: MAX-PLANCK-GESELLSCHAFT ZUR FÖRDERUNG DER WISSENSCHAFTEN E.V., Munich (DE)

(72) Inventors: Andreas J. Vorholt, Mülheim an der Ruhr (DE); Walter Leitner, Mülheim an der Ruhr (DE); Thiemo Faßbach, Mülheim an der Ruhr (DE); Paul Kossmann, Mülheim an der Ruhr (DE)

(73) Assignee: MAX-PLANCK-GESELLSCHAFT ZUR FÖRDERUNG DER WISSENSCHAFTEN E.V., Munich (DE)

( * ) Notice: Subject to any disclaimer, the term of this patent is extended or adjusted under 35 U.S.C. 154(b) by 502 days.

(21) Appl. No.: 18/574,693

(22) PCT Filed: Jun. 28, 2021

(86) PCT No.: PCT/EP2021/067662
§ 371 (c)(1),
(2) Date: Dec. 27, 2023

(87) PCT Pub. No.: WO2023/274492
PCT Pub. Date: Jan. 5, 2023

(65) Prior Publication Data
US 2024/0336561 A1 Oct. 10, 2024

(51) Int. Cl.

| | |
|---|---|
| ***C07D 263/12*** | (2006.01) |
| ***B01J 31/18*** | (2006.01) |
| ***B01J 31/20*** | (2006.01) |
| ***B01J 31/24*** | (2006.01) |
| ***C07C 263/12*** | (2006.01) |

(52) U.S. Cl.
CPC ........... *C07C 263/12* (2013.01); *B01J 31/189* (2013.01); *B01J 31/20* (2013.01); *B01J 31/2409* (2013.01); *B01J 2231/763* (2013.01); *B01J 2531/004* (2013.01); *B01J 2531/821* (2013.01)

(58) Field of Classification Search
CPC ............... C07C 263/12; B01J 2231/763; B01J 2531/821; B01J 31/20
See application file for complete search history.

(56) References Cited

U.S. PATENT DOCUMENTS

| | | | | |
|---|---|---|---|---|
| 3,960,914 | A | 6/1976 | Lyons | |
| 4,207,251 | A | 6/1980 | Heyboer | |
| 4,469,640 | A | 9/1984 | Carcia et al. | |
| 4,537,726 | A | 8/1985 | Rao et al. | |
| 4,683,329 | A | 7/1987 | Rao | |
| 5,155,267 | A * | 10/1992 | Faraj | C07C 269/00 564/48 |
| 9,156,948 | B2 * | 10/2015 | Brandstadt | C08L 83/04 |
| 10,562,767 | B2 * | 2/2020 | Milstein | C01B 3/0015 |
| 2012/0253063 | A1 | 10/2012 | Mattke et al. | |
| 2015/0104371 | A1 * | 4/2015 | Peters | C01C 1/026 423/407 |
| 2017/0283447 | A1 * | 10/2017 | Milstein | C07C 249/02 |
| 2023/0374195 | A1 * | 11/2023 | Schaub | B01J 31/189 |

FOREIGN PATENT DOCUMENTS

| | | | |
|---|---|---|---|
| CN | 102666479 | A | 9/2012 |
| DE | 3229323 | A1 | 2/1984 |

OTHER PUBLICATIONS

J. Bruffaerts et al., 141 Journal of the American Chemical Society, 16486-16493 (2019) (Year: 2019).*
S. Kim et al., 18 Organic Letters, 212-215 (2016) (Year: 2016).*
S. Kotachi et al, Journal of the Chemical Society, Chemical Communications, 549-550 (1990) (Year: 1990).*
E. Lane et al., 9 Chemical Science, 4003-4008 (2018) (Year: 2018).*
Bruffaerts et al., "Formamides as Isocyanate Surrogates: A Mechanistically Driven Approach to the Development of Atom-Efficient, Selective Catalytic Syntheses of Ureas, Carbamates, and Heterocycles," *J. Am. Chem,. Soc.* 141:16486-16493, Sep. 18, 2019. (8 pages).
Fu et al., "Dehydrogenation of Secondary Formamides," *J. Chem. Soc., Perkin Trans.* 1:2246-2250, Jan. 1, 1974. (5 pages).
Kondo et al., "Novel Ruthenium-Complex-Catalyzed Synthesis of Ureas from Formamides and Amines," *Organometallics* 16:2562-2570, Jun. 10, 1997. (9 pages).
Kotachi et al., "Ruthenium catalysed N,N"-Diarylurea Synthesis from N-Aryl substituted Formamides and Aminoarenes," *J. Chem. Soc., Chem. Commun*:549-550, Jan. 1, 1990. (2 pages).
Kotachi et al., "Ruthenium complex-catalyzed synthesis of carbamates by dehydrogenative reaction of formamides with alcohols," *Catalysis Letters* 19:339-344, Dec. 1993. (6 pages).
Lane et al., "Iron-catalyzed urea synthesis: dehydrogenative coupling of methanol and amines," *Chem. Sci.* 9:4003-4008, Apr. 28, 2018 [Published online Apr. 9, 2018]. (6 pages).
Schwetlick et al., "Synthesis of isocyanates by catalytic dehydrogenation of formamides and oxamides," *Chem* 14:192, 1974. (with English Translation) (3 pages).

* cited by examiner

*Primary Examiner* — Alexander R Pagano
(74) *Attorney, Agent, or Firm* — Seed Intellectual Property Law Group LLP

(57) ABSTRACT

The present invention is directed towards a process for the preparation of free isocyanates, which improves upon the disadvantages associated with heterogeneous catalysis. The process comprises converting formamides into the corresponding isocyanates via a catalytic dehydrogenation, which involves bringing the formamide into contact with a Group VII, VIII or IX transition metal complex and heating.

20 Claims, No Drawings

CATALYTIC SYNTHESIS OF FREE ISOCYANATES

FIELD OF THE INVENTION

The present invention is directed towards a process for the preparation of free isocyanates. In particular, the invention is directed towards converting formamides into the corresponding isocyanates via a catalytic dehydrogenation process.

BACKGROUND OF THE INVENTION

In recent years the market for plastics has rapidly expanded. Industries have become reliant on these materials (in particular polyurethane), as a result of their favourable and varied properties. The production of polyurethane (PU) typically involves diols or polyols and diisocyanates or polyisocyanates. The synthesis of such isocyanates is key, as industrial production methods to-date utilise the highly toxic reagent phosgene and result in large quantities of hydrochloric acid by-products.

In order to avoid such disadvantages, the present inventors sought after a greener and cleaner synthesis route. This alternative route involves the catalytic synthesis of isocyanates from formamides. The synthesis of formamides from amines has previously been reported and involves the use of carbon dioxide and hydrogen, with loss of water.

Various processes have been developed to convert formamides to isocyanates, but these processes involve heterogeneous catalysis and typically occur under oxidative conditions. Such reactions are described in U.S. Pat. Nos. 4,207,251, 4,469,640, 4,537,726, 4,683,329 and DE 32 29 323.

Some heterogenous reactions to convert amides to isocyanates which do not specifically occur under oxidative conditions have also been described in the literature. For example, U.S. Pat. No. 3,960,914 the conversion of formamides to isocyanates in the presence of ruthenium black, platinum black, palladium black, or any one of ruthenium, platinum or palladium on a suitable support such as carbon, alumina, kieselguhr, corhart, or the like. Further examples of such dehydrogenation reactions are described in *J.C.S. Perkin I,* 1974, 2246-2250 (Fu, P. P.; Boyer, J. H.), and in *Z. Chem.,* 14, 1974, Heft 5, 192 (Schwetlick, K.; Kretzschmar, F.).

An advantage of heterogeneous catalysis can be the more facile isolation and recovery of the product. However, in comparison to homogeneous catalysis, heterogeneous catalysis is associated with a variety of disadvantages. These include lack of product selectivity, smaller variety in reaction conditions, higher sensitivity towards poisons and less variability of steric and electronic properties.

Thus, the present inventors focused on developing a synthetic strategy involving homogeneous catalysis for the conversion of formamides to free isocyanates.

A number of processes involving amide starting materials and homogeneous catalysis exist, however these are directed towards converting amides to ureas and/or carbamates, not isocyanates.

For example, Lane, E. M.; Hayari, N. and Bernskoetter, W. H. (*Chem. Sci.,* 2018, 9, 4003-4008) describe an iron-catalysed urea synthesis. The process involves the dehydrogenative coupling of methanol and amines using a pincer supported iron catalyst, to form the corresponding urea products.

Bruffaerts, J.; von Wolff, N.; Diskin-Posner, Y.; Ben-David, Y. and Milstein, D. (*J. Am. Chem. Soc.* 2019, 141, 16486-16493) describe a catalytic, isocyanate-free process for the synthesis of ureas, carbamates and heterocycles. The process generally involves the reaction of substituted formamides with a ruthenium-based pincer complex and a nucleophile, to produce the desired products.

Further homogeneous catalysis reactions converting formamides to carbamates/ureas are described in U.S. Pat. No. 5,155,267 and in *Catalysis Letters,* 19, 1992, 339-334 (Kotachi, S.; Kondo, T.; Watanabe, Y.).

Further processes for the synthesis of ureas from formamides and amines are described in *Organometallics,* 16, 1997, 2562-2570 (Kondo, T.; Kotachi, S.; Tsuji, Y.; Watanabe, Y.; Mitsudo, T.) and in *J. Chem. Soc., Chem. Commun.,* 1990, 549-550 (Kotachi, S.; Tsuji, Y.; Kondo, T.; Watanabe, Y.).

It is an object of the present invention to provide a process for the preparation of free isocyanate, which improves upon the disadvantages associated with heterogeneous catalysis. In particular, the present invention allows for the production of free isocyanates in good yields and with good product selectivity. In addition to free isocyanates, the reaction according to the present invention yields $H_2$. The process according to the present invention involves the conversion of a formamide into the corresponding isocyanate via a catalytic dehydrogenation reaction.

SUMMARY OF THE INVENTION

The above object is solved by a process for the preparation of free isocyanate as defined in claim 1. Preferred embodiments of the process are the subject of the dependent claims.

DETAILED DESCRIPTION

Embodiments according to the present invention will now be described in more detail.

As used herein, “Ph” refers to a phenyl group, “$^{i}$Pr” refers to an iso-propyl group, “$^{t}$Bu” refers to a tert-butyl group and “Et” refers to an ethyl group.

As used herein, the term “free isocyanate” refers to the isocyanate which corresponds to the formamide starting material (see FIGURE below). The free isocyanate is not bound, in particular not covalently bound, or complexed to any additional elements or compounds (such as the catalyst).

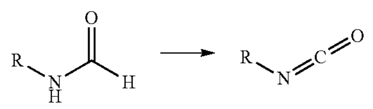

The term “pincer ligand” refers to a tridentate ligand. Examples of pincer ligands include, but are not limited to the following:

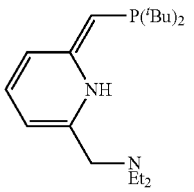

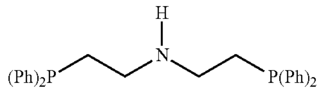

Pincer ligands can be labelled by naming them according to the atoms interacting with the metal centre, such that the first compound in the above FIGURE is referred to as a PNN-type pincer ligand and the second compound is referred to as a PNP-type pincer ligand.

The term "non-innocent ligand" refers to a ligand which can take part in a reaction to be catalysed by a transition metal catalyst comprising the non-innocent ligand. For example, a non-innocent ligand could undergo a deprotonation during the reaction, forming a basic site on the ligand which has the ability to abstract a proton from the substrate. A non-innocent redox-ligand, for example, could function as an electron reservoir, such that the oxidation state of the metal does not change during the catalytic cycle.

The reaction according to the invention is a catalytic dehydrogenation of formamides to isocyanates (see FIGURE below). Throughout the reaction, free isocyanate, i.e., isocyanate that is not covalently bonded to any additional elements or compounds, is released and the transition metal catalyst is regenerated. It was generally confirmed by High-Resolution Mass Spectrometry (HRMS) that the free isocyanate was obtained. The free isocyanate can be isolated and characterised utilising suitable methods.

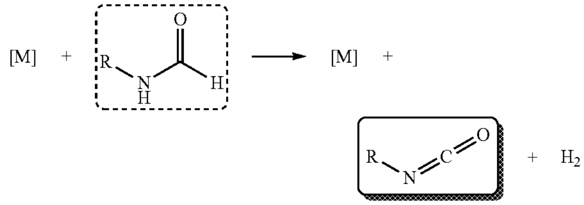

A process according to the present invention includes converting a formamide into the corresponding isocyanate by catalytic dehydrogenation, wherein the formamide is brought into contact with a catalyst and is heated, wherein the catalyst is a Group VII, VIII or IX transition metal complex.

In a preferred embodiment, the formamide is a secondary amide.

The process according to the invention can be used for the preparation of free isocyanate, wherein the isocyanate can be a monoisocyanate, a diisocyanate, or a polyisocyanate.

When the isocyanate is a monoisocyanate, the monoisocyanate is preferably of the formula $R_1-(CH_2)_w-NCO$, wherein:

$R_1$ is a C1-C4 linear or branched alkyl, or a C5-C10 aryl; and w is an integer of 0-3;

preferably $R_1$ is phenyl or tert-butyl, and w is an integer of 0-3.

The corresponding formamide can, for example be

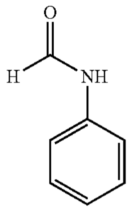
,
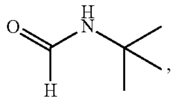
, or

-continued

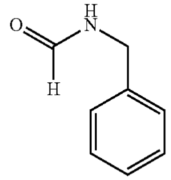
; preferably
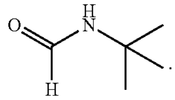
.

When the isocyanate is a monoisocyanate, the monoisocyanate is more preferably butylisocyanate.

preferred embodiment, the free isocyanate is a diisocyanate.

When the isocyanate is a diisocyanate, the diisocyanate is preferably of the formula $OCN-(R_2)_x-(R_4)_a-(CH_2)_z-(R_5)_b-(R_3)_y-NCO$, wherein:

each $R_2$ and $R_3$ are independently $-CH_2-$, $-CH(CH_3)-$ or $-C(CH_3)_2-$;

each x and y are independently an integer of 0-5;

each $R_4$ and $R_5$ are independently a C3-C8 cyclic alkylene or C5-C10 arylene, each optionally substituted with one or more $-CH_3$ groups;

each a and b are independently an integer of 0 or 1;

and z is an integer of 0-2.

When the isocyanate is a diisocyanate, the diisocyanate is more preferably hydrogenated MDI (also known as 4,4'-diisocyanato dicyclohexylmethane or bis(4-isocyanatocyclohexyl) methane) (H12MDI), hexamethylene diisocyanate (HDI), isophorone diisocyanate (IPDI), 4,4'-methylene diphenyl diisocyanate (MDI), 2,4'-MDI, 2,2'-MDI, m-xylylene diisocyanate (m-XDI), p-xylylene diisocyanate (p-XDI), m-tetramethylxylene diisocyanate (m-TMXDI), p-tetramethylxylene diisocyanate (p-TMXDI), 1,5-naphthylene diisocyanate (NDI), 2,4-toluene diisocyanate (2,4-TDI), or 2,6-toluene diisocyanate (2,6-TDI).

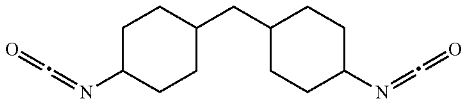

Bis(4-isocyanatocyclohexyl) methane

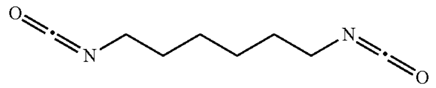

1,6-diisocyanatohexane (HDI)

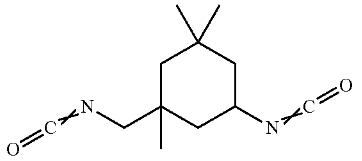

Isophorondiisocyanat

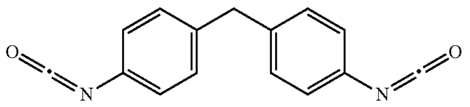

4,4′-Methylendiphenylisocyanate

-continued

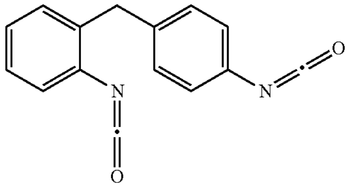

2,4'-Methylendiphenylisocyanate

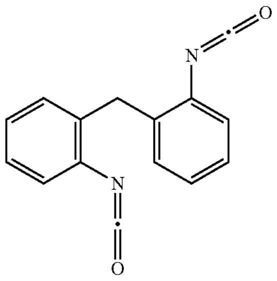

2,2'-Methylendiphenylisocyanate

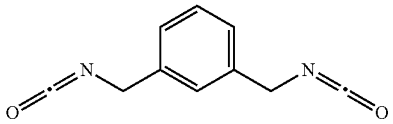

meta Xylene Diisocyanate

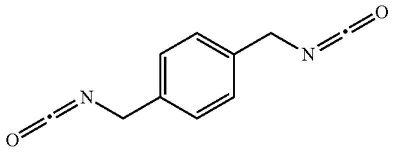

para Xylene Diisocyanate

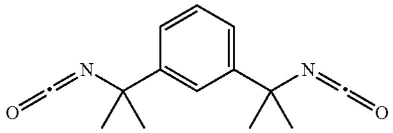

meta-Tetramethyl Xylene Diisocyanate

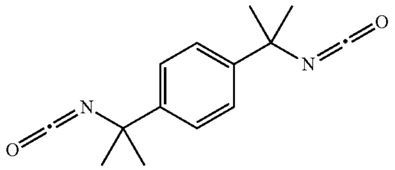

para-Tetramethyl Xylene Diisocyanate

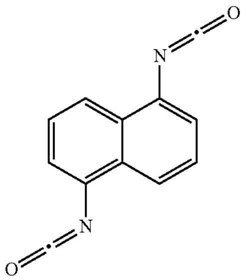

Naphtylene diisocyanate

-continued

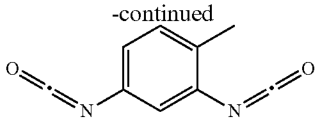

2,4-Toluenediisocyanate

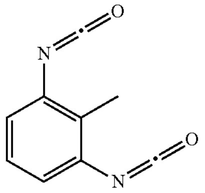

2,6-Toluenediisocyanate

Most preferably the diisocyanate is HDI, H12MDI or 2,4-TDI.

In a preferred embodiment according to the present invention, a process for the preparation of free isocyanate is a homogeneous catalytic process.

According to a preferred embodiment of the invention, the process comprises the release of hydrogen.

In a further preferred embodiment, the catalytic dehydrogenation is a non-oxidative catalytic dehydrogenation.

In a preferred embodiment, the process takes place under inert atmosphere.

According to a preferred embodiment of the invention, when the formamide is brought into contact with a catalyst and is heated, the temperature is preferably between 100-250° C. More preferably the temperature is between 160-240° C., even more preferably between 165-240° C., even more preferably between 170-240° C., even more preferably between 175-235° C., even more preferably between 180-230° C., even more preferably between 185-225° C. Most preferably, the temperature is between 190-220° C.

The process according to the invention can be carried out in any means suitable, preferably in an autoclave reactor or a microwave. Based on the knowledge of the micro kinetics of the reaction, the skilled person would use suitable reactor types.

In a preferred embodiment, the formamide and the catalyst are heated, preferably at a temperature of between 190-220° C., for between 0.5-48 hours, more preferably 1-36 hours, even more preferably 1-24 hours, even more preferably 1-16 hours, even more preferably 1-12 hours, even more preferably 1-8 hours, most preferably 1-4 hours.

The process according to the invention can be carried out in neat conditions or in the presence of one or more solvents. In a preferred embodiment, the conversion of the formamide to the corresponding isocyanate takes place in a solvent. Preferably, the solvent is an aprotic solvent. This has the advantage that it avoids the conversion of the product into unwanted side-products. A further advantage is that dehydrogenation of the solvent cannot occur, which would be a competing reaction to the dehydrogenation of the formamide. When the solvent is an aprotic solvent, the solvent is preferably an aromatic hydrocarbon or an ether. When the solvent is an aromatic hydrocarbon or an ether, the solvent is preferably toluene, dioxane or cyclopentyl methyl ether (CPME), more preferably CPME.

The process according to the invention involves a catalyst, wherein the catalyst is a Group VII, VIII or IX transition metal complex.

According to an embodiment of the invention, the catalysis is based on a metal-ligand cooperation (MLC). MLC involves metal-ligand complexes which form a bi-functional system. Such systems are typically more active than classical metal catalysts. The design of the ligands used in the bi-functional system, allow the electronic and structural properties of the transition metal to be varied. Furthermore, the ligands can actively participate in the key bond-forming and/or bond-breaking steps.

Different strategies can be applied in order to increase the activity of the catalysts and/or to change the structure and electronic properties of the metal centre. For example, the ligands can i) act as Lewis bases, ii) act as Lewis acids, iii) be aromatised/de-aromatised during the reaction, or iv) act as non-innocent redox-ligands.

In a preferred embodiment, the transition metal complex contains a non-innocent ligand. For example, the non-innocent ligand is a ligand capable of undergoing de-aromatisation upon deprotonation.

In a preferred embodiment, the transition metal complex contains a pincer ligand. This has the advantage that the pincer ligand allows the thermal stability of the catalyst to be increased. This is particularly helpful since acceptor-less dehydrogenation reactions require higher reaction temperatures. Preferably, the pincer ligand is a PNP-type pincer ligand or a PNN-type pincer ligand. More preferably, the pincer ligand is a PNP-type pincer ligand.

In a more preferred embodiment the ligand is a pincer ligand and a non-innocent ligand. Examples of such ligands include, but are not limited to, the following:

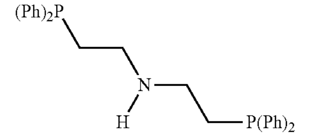

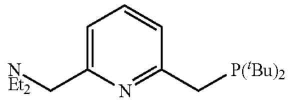

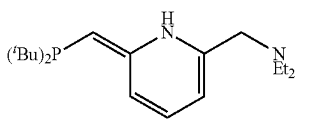

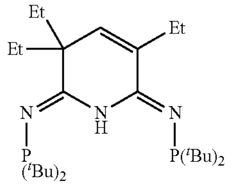

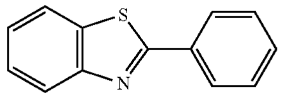

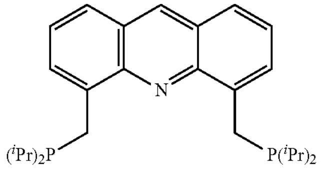

Most preferably, the pincer ligand that is also a non-innocent ligand is:

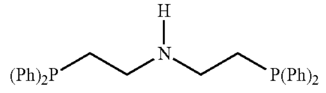

-continued

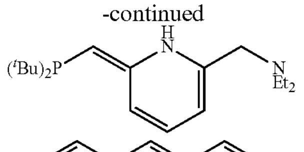

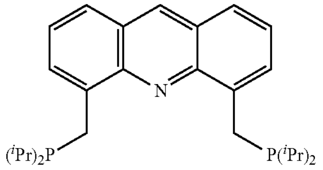

In a preferred embodiment, the transition metal of the transition metal complex is Ru, Fe, Mn, or Ir. More preferably, the transition metal is Ru.

In a preferred embodiment according to the invention, the transition metal complex is of the formula

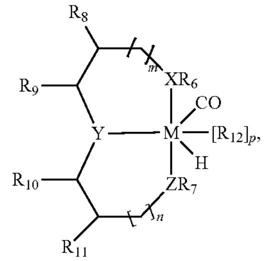

wherein:

- M is a Group VII, VIII or IX transition metal, preferably Ru, Fe, Mn, or Ir, most preferably Ru;
- each X, Y and Z are independently P, N, or C;
- each $R_6$ and $R_7$ are independently -$Ph_2$, —($^i$Pr)$_2$, —($^t$Bu)$_2$ or —$Et_2$;
- each $R_8$ and $R_9$ are independently H, a C1-C10 alkyl, or a C5-C10 aryl;
- each $R_{10}$ and $R_{11}$ are independently H, a C1-C10 alkyl, or a C5-C10 aryl;
- each m and n are independently an integer of 0-3;
- p is 0 or 1; and
- when p is 1, $R_{12}$ is Cl;
- wherein optionally:
- the carbon attached to $R_8$ forms a double bond with the carbon attached to $R_9$; and/or
- the carbon attached to $R_{10}$ forms a double bond with the carbon attached to $R_{11}$; and/or
- two or more of $R_8$, $R_9$, $R_{10}$, and $R_{11}$ form a ring system, wherein the ring system is preferably an aromatic $C_3$-$C_6$ monocyclic ring system, or an aromatic $C_{9-14}$ tricyclic ring system; and/or
- the carbon attached to $R_9$ forms a double bond with Y; and/or
- the carbon attached to $R_{10}$ forms a double bond with Y.

In a more preferred embodiment, the transition metal complex is

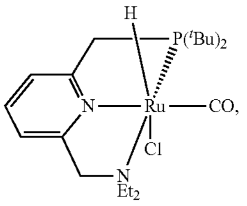

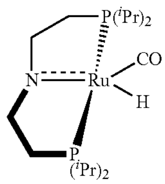

,

I

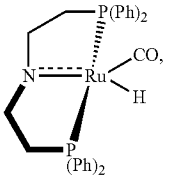

II

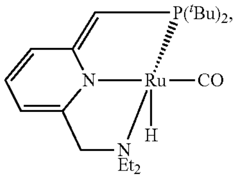

or

III

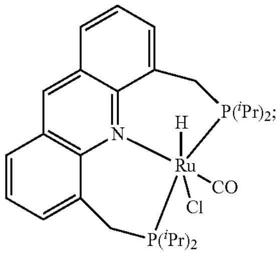

I

Preferably

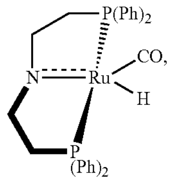

II

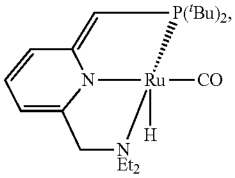

or

III

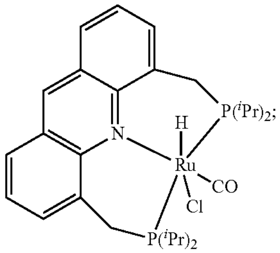

-continued

II more preferably

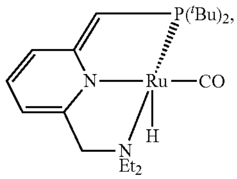

or

III

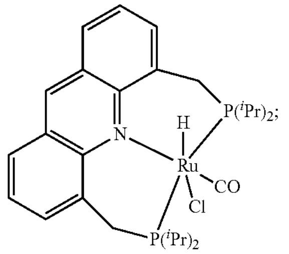

III most preferably

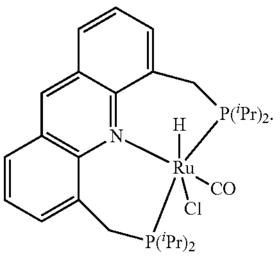

The present invention includes the use of the aforementioned catalysts I, II, and/or III as dehydrogenation catalysts in the formation of free isocyanate.

According to a preferred embodiment of the present invention, the concentration of the transition metal complex in relation to the formamide is from 0.01 to 1 mol %.

In an embodiment, the process according to the present invention can provide a yield of more than 20% of the product.

In an embodiment, the process according to the present invention can provide a selectivity of more than 60%.

In an embodiment, the process according to the present invention can provide a selectivity of more than 60% and a yield of more than 20% of the product.

In a most preferred embodiment, the process for the preparation of free isocyanate comprises converting a formamide into the corresponding free isocyanate by catalytic dehydrogenation,

- wherein the formamide is brought into contact with a catalyst and is heated between 170-240° C. in a solvent, preferably toluene, dioxane or CPME, most preferably CPME;
- wherein the catalyst is a Group VII, VIII or IX transition metal complex;
- wherein the transition metal is preferably Ru, Fe, Mn or Ir, most preferably Ru;
- wherein the transition metal complex comprises a ligand that is both a pincer ligand and a non-innocent ligand;
- wherein the catalytic process for the preparation of the free isocyanate is a homogenous catalytic process;
- wherein the process comprises the release of hydrogen;
- wherein the isocyanate is a monoisocyanate, a diisocyanate or a polyisocyanate, preferably a diisocyanate; and
- wherein the process takes place under inert atmosphere.

According to a further embodiment of the invention, the conversion of the formamide to the corresponding isocyanate takes place in the presence of an additive. The additive is preferably a base, an acid, or a hydrogen scavenger. The additive may simultaneously function as a solvent.

When the additive is a base, the additive is preferably 1,8-diazabicyclo [5.4.0]undec-7-ene (DBU), 1,5-diazabicyclo [4.3.0]non-5-ene (DBN), 1,4-diazabicyclo [2.2.2]octane (DABCO) or an alkylamine, more preferably DBU.

When the additive is an acid, the additive is preferably p-toluenesulfonic acid (p-TsOH).

When the additive is a hydrogen scavenger (or hydrogen acceptor), it should be a molecule with at least one structure or functional group that can accept a hydrogen molecule. This acceptance can be, in general terms, a hydrogenation. Having more than one of these hydrogen accepting structures may be advantageous. In the best case, this hydrogen accepting structure should be a C/C double or triple bond. Other functional groups or structures that can accept the hydrogen are also possible, provided the resulting protic structure does not react with the product. The remaining part of the molecular structure may also consist of carbon or even heteroatoms. For example, this may include aliphatic, cyclic or aromatic carbons. The hydrogen acceptor is at least a $C_2H_2$ molecule. Preferably, the hydrogen scavenger is an olefin, more preferably a $C_2$-$C_{20}$ olefin, even more preferably a $C_2$-$C_{10}$ olefin, most preferably 3,3-dimethylbutene (neo-hexene). The addition of a hydrogen scavenger has the advantage that the yield of the product can be improved.

In an embodiment according to the invention, the mole ratio between the amide and the additive ranges from catalytic amounts to super stoichiometric amounts.

Overall, the methods described herein have a number of advantages. The present invention provides a process for the preparation of free isocyanate, which improves upon the disadvantages associated with heterogeneous catalysis. In particular, these advantages include but are not limited to the production of free isocyanates in good yields and with good product selectivity. The process according to the present invention (conversion of a formamide into the corresponding isocyanate via a catalytic dehydrogenation reaction) also yields $H_2$.

EXAMPLES

Examples according to the present invention will be presented. The following general procedure was utilised to complete the experiments and form the isocyanate product:

The starting material and the catalyst are dissolved in the solvent under inert atmosphere, placed into the reactor (e.g., an autoclave or microwave) and heated to the desired temperature for the desired time.

For analytical purposes, the isocyanate product is transformed into the corresponding carbamate. This has the advantage that the carbamate is easier to quantify and is less toxic. The carbamate is synthesised as follows:

To the above reaction mixture (once the desired reaction time is complete), methanol is added and the mixture is heated to the desired temperature for the desired time. A sample is then taken from the resulting reaction mixture and quantitative data is obtained using GC-FID and an internal standard (e.g., tetradecane).

For the analysis of the reaction mixtures and the collection of quantitative data, a calibration was carried out in advance. First, a series of separate solutions at different concentrations of each of the individual substrates were prepared. The same amount of an internal standard (for example tetradecane), was added to each concentration mixture. Each of these mixtures was measured on the same device with the same set-up and temperature profile. The linear relationship between the areas under the curve of the substance to be analysed and the internal standard and the respective concentrations was determined (using the software LabSolutions). The linear relationship was then utilised to determine the concentration of the compounds in question (the product in the reaction mixture).

In order to exclude the possibility that the methanol contributes to the conversion of the formamide to the isocyanate, a series of experiments were completed in the presence of methanol but the absence of the transition metal complex (the catalyst). These experiments confirmed that the carbamate is not formed in the absence of the transition metal complex.

Gas chromatography-mass spectrometry (GC-MS) was conducted using a Shimadzu GCMS-QP2020 Gas Chromatograph Mass Spectrometer. The column was of the type RTX1 30 m, 0.25 mm, 0.5 μm; the name of the column used is S88, 1413000; and the gas used was helium. Gas chromatography with flame-ionisation detection (GC-FID) was conducted using a Shimadzu Nexis GC-2030 Gas Chromatograph. The column was of the type RTX-1, 30 m, 0.25 mm, 0.5 μm; the name of the column used is S114; and the gas used was helium. Experiments which were conducted in an autoclave, were conducted in a stainless steel autoclave with a volume of 10 mL. Experiments which were conducted in a microwave, were conducted in an Anton Paar Monowave 450. 10 mL Anton Paar microwave vials with cap and PTFE septum were used.

Specific examples of reactions according to the invention will now be discussed and presented in the following tables. The above discussed general procedures were applied, utilising the conditions specified in each of the tables and their titles.

The below table 1 shows the data for experiments carried out according to the present invention, utilising various starting materials, catalysts and reaction conditions.

The tested catalysts include catalyst I, catalyst II and catalyst III:

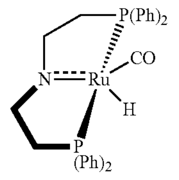

I

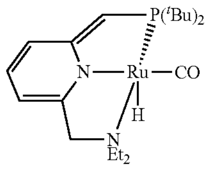

II

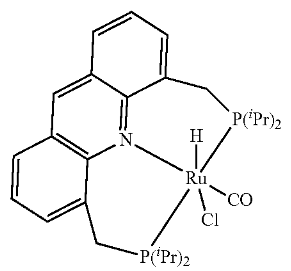

III

It is noted that catalyst I was prepared ex situ from complex $I^{prime}$ as shown in the FIGURE below. First, $^{t}$BuOK was filled into a Schlenk finger. Complex $I^{prime}$ was filled into another Schlenk finger and dissolved in dry THF. Subsequently, the THF solution was transferred via a cannula into the first Schlenk finger and then stirred for 1 hour at room temperature. After the reaction time, the solvent was removed in vacuo under inert atmosphere. The residues were then dissolved in toluene and filtered under inert atmosphere. The gained solution was concentrated in vacuo to obtain catalyst I.

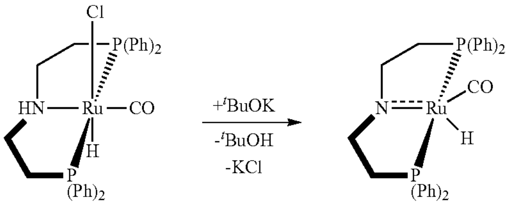

$I^{prime}$ I

TABLE 1

Process according to the invention. General reaction conditions: the reactions were completed in an autoclave; the solvent added was toluene (2 mL); the starting material (SM), the catalyst (Cat), temperature (Temp), and reaction time (time in hours) are specified in the table. 4 mmol of neo-hexene were added to the reaction mixture prior to heating. The % conversion (Conv), % yield and % selectivity (Selec) were calculated based on the carbamate resulting from reacting the isocyanate with 1.5 mL of methanol for 5 hours at 160 °C

| # | SM (mmol) | Cat (mol %) | Temp (°C) | Time (hrs) | Yield (%) |
|---|---|---|---|---|---|
| 1 | Formanilide (4 mmol) | I (0.5) | 160 | 16 | 9 |
| 2 | Formanilide (4 mmol) | II (0.5) | 160 | 16 | 5 |
| 3 | Formanilide (4 mmol) | III (0.5) | 160 | 16 | 13 |
| 4 | Formanilide (4 mmol) | II (0.5) | 100 | 16 | 1 |
| 5 | Formanilide (4 mmol) | II (0.5) | 130 | 16 | 2 |
| 6 | Formanilide (4 mmol) | II (0.5) | 160 | 16 | 5 |
| 7 | Formanilide (4 mmol) | II (0.5) | 190 | 16 | 9 |
| 8 | Formanilide (4 mmol) | II (0.5) | 160 | 24 | 5 |
| 9 | Formanilide (4 mmol) | II (0.5) | 160 | 72 | 8 |
| 10 | Formanilide (4 mmol) | II (0.5) | 160 | 96 | 9 |
| 11[a] | Formanilide (4 mmol) | II (0.5) | 160 | 16 | 4 |
| 12[b] | Formanilide (4 mmol) | I (0.5) | 190 | 16 | 9 |
| 13[b] | Formanilide (4 mmol) | III (0.5) | 190 | 16 | 13 |

[a]Toluene was replaced by xylene (2 mL) as the solvent

[b]The % conversion (Conv), % yield and % selectivity (Selec) were calculated based on the carbamate resulting from the reaction of the isocyanate with 1 mL of methanol for 1 hour at 190 °C Furthermore, the following reactions were also carried out:

Following the abovementioned general experimental procedure, a reaction using

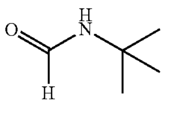

as the starting material (4 mmol) and a separate reaction using

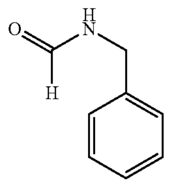

as the starting material (4 mmol) were completed in an autoclave. The solvent added was toluene (2 mL), the catalyst used was catalyst II (0.5 mol %), the temperature at which the reaction was run was 190° C. and the reaction time for each experiment was 19 hours. 4 mmol of neo-hexene were added to the reaction mixture prior to heating. Upon completion of the reaction time, the GC-MS data indicated that the corresponding free isocyanate was formed.

Further experiments according to the present invention utilising formanilide as the starting material were completed. The corresponding data is presented in the below table (table 2).

TABLE 2

Process according to the invention utilising formanilide as the starting material. General reaction conditions: reaction was completed in a microwave; starting material (SM) is formanilide; catalyst (Cat) is catalyst III; % conversion (Conv) , % yield and % selectivity (selec) were calculated based on the carbamate resulting from reaction of the isocyanate with 1 mL of methanol for 1 hour at the same temperature as that utilised for the production of the isocyanate (column 'Temp' in below table). The remaining reaction conditions are listed in the table.

| # | SM (mmol) | Solvent | Temp (°C) | Time (hours) | Cat (mol %) | Yield (%) | Selec (%) |
|---|---|---|---|---|---|---|---|
| 1 | 4 | Toluene (2 mL) | 190 | 4 | 1 | 19 | 43 |
| 2 | 4 | Toluene (1 mL) | 160 | 4 | 0.5 | 26 | 51 |
| 3 | 4 | Dioxane (2 mL) | 160 | 4 | 0.25 | 10 | 84 |
| 4 | 4 | Dioxane (2 mL) | 160 | 8 | 0.125 | 9 | 62 |

Further experiments according to the present invention utilising formanilide as the starting material were completed. The corresponding data is presented in the below table (table 3). Unless stated otherwise in the table, the following procedure (in accordance with the general procedure outlined above) was applied:

During the process according to the invention, formanilide and the catalyst III were dissolved in a solvent (2 mL) under inert atmosphere in a microwave-vial. The vial was placed in the microwave and heated for 4 hours. For analytical purposes, upon completion of the 4 hours, methanol (1.5 mL) was added to the vial. The vial was heated to 190° C. for 1 hour. Following this, a sample was taken from the vial and analysed via GC-FID.

TABLE 3

Process according to the invention utilising formanilide as the starting material. General reaction conditions: reaction was completed in a microwave; starting material (SM) is formanilide; catalyst (Cat) is catalyst III; reaction time is 4 hours; % conversion (Conv), % yield and % selectivity (selec) were calculated based on the carbamate resulting from reaction of the isocyanate with 1.5 mL of methanol for 1 hour at 190 °C The remaining reaction conditions are listed in the table.

| # | SM (mmol) | Solvent (2 mL) | Temp (°C) | Cat (mol %) | Conv (%) | Yield (%) | Selec (%) |
|---|---|---|---|---|---|---|---|
| 1 | 0.5 | CPME | 220 | 0.25 | 89 | 45 | 51 |
| 2 | 0.75 | CPME | 220 | 0.25 | 88 | 28 | 32 |
| 3 | 1.5 | CPME | 220 | 0.25 | 75 | 20 | 27 |
| 4 | 1.75 | CPME | 220 | 0.25 | 73 | 19 | 26 |
| 5 | 2 | Dioxane | 160 | 0.25 | 22 | 9 | 42 |
| 6 | 2 | Dioxane | 180 | 0.25 | 23 | 10 | 45 |
| 7 | 2 | Dioxane | 200 | 0.25 | 77 | 18 | 24 |
| 8 | 2 | Dioxane | 220 | 0.25 | 66 | 17 | 26 |
| 9 | 2 | Dioxane | 235 | 0.25 | 73 | 15 | 20 |
| 10 | 2 | Dioxane | 250 | 0.25 | 77 | 14 | 18 |
| 11 | 2 | THE | 180 | 0.25 | 21 | 9 | 43 |
| 12 | 2 | CPME | 180 | 0.25 | 29 | 10 | 35 |
| 13 | 2 | 2-Methyl-THF | 180 | 0.25 | 25 | 12 | 47 |
| 14 | 2 | ACN | 180 | 0.25 | 21 | 6 | 28 |
| 15 | 2 | Pyridine | 180 | 0.25 | 25 | 8 | 33 |
| 16 | 2 | TEA | 180 | 0.25 | 66 | 14 | 21 |
| 17 | 2 | 2-Methyl-THF | 220 | 0.25 | 68 | 19 | 28 |
| 18 | 2 | Pyridine | 220 | 0.25 | 59 | 18 | 30 |
| 19 | 2 | CPME | 220 | 0.25 | 69 | 18 | 26 |
| 20 | 4 | CPME | 220 | 0.0125 | 26 | 2 | 7 |
| 21 | 1 | CPME | 220 | 0.25 | 63 | 30 | 47 |
| 22 | 1 | CPME | 220 | 0.5 | 67 | 29 | 42 |
| 23 | 1 | CPME | 220 | 0.75 | 90 | 27 | 30 |
| 24 | 1 | CPME | 220 | 1 | 92 | 25 | 27 |
| 25[a] | 2 | Dioxane | 190 | 0.25 | 81 | 16 | 22 |
| 26[b] | 2 | Dioxane | 190 | 0.25 | 62 | 24 | 40 |
| 27[c] | 0.5 | CPME | 220 | 0.25 | 46 | 31 | 83 |
| 28[d] | 2 | Dioxane | 190 | 0.25 | 20 | 13 | 66 |
| 29[e] | 4 | Toluene | 190 | 0.5 | 28 | 16 | 25 |
| 30[e] | 4 | Toluene | 160 | 0.5 | 46 | 15 | 34 |

[a]The reaction was run in the presence of 30 μl of DBU.

[b]The reaction was run in the presence of 3 μl of DBU.

[c]The reaction was run in 1.55 mL of solvent instead of 2 mL.

Furthermore, % conversion, % yield and % selectivity were calculated based on the carbamate resulting from reaction of the isocyanate with 1.5 mL of methanol for 1 hour at room temperature.

[d]% conversion, % yield and % selectivity were calculated based on the carbamate resulting from reaction of the isocyanate with 1.5 mL of methanol for 1 hour at 160 °C.

[e]The reaction was run utilising catalyst II instead of III.

Furthermore, % conversion, % yield and % selectivity were calculated based on the carbamate resulting from reaction of the isocyanate with 1 mL of methanol for 1 hour at 190 °C.

Experiments for several diisocyanate products were also completed. The data in the below table (table 4) was acquired by utilising the corresponding formamide of each of HDI, H12MDI and 2,4-TDI. The specific reaction conditions were as follows:

The starting material (1 mmol) and catalyst III (0.25 mol %) were dissolved in CPME (2 mL) under inert atmosphere in a microwave-vial. The vial was placed in the microwave and heated to 220° C. for 4 hours.

For analytical purposes, upon completion of the 4 hours, methanol (1.5 mL) was added to the vial. The vial was heated to 190° C. for 1 hour. Following this, a sample was taken from the vial and analysed via GC-FID.

TABLE 4

Process according to the invention, producing various diisocyanates. General reaction conditions: the reaction was completed in a microwave; the catalyst is catalyst III (0.25 mol %); the temperature was 220 °C, the solvent was CPME (2 mL), the amount of starting material added was 1 mmol, the reaction time was 4 hours. The % conversion, % yield and % selectivity were calculated based on the carbamate resulting from reacting the diisocyanate with 1.5 mL of methanol for 1 hour at 190 °C

| # | Product | Conversion (%) | Yield (%) | Selectivity (%) |
|---|---|---|---|---|
| 1 | HDI | 23 | 7 | 32 |
| 2 | H12MDI | 36 | 22 | 62 |
| 3 | 2,4-TDI | 74 | 17 | 22 |

As a precipitate was observed prior to removing a sample for GC-FID analysis, it is noted that the percentages provided in the above table 4 should be considered as the minimum values achievable. Some of the product may have precipitated prior to analysis and could thus not be considered towards the final data in the table. Therefore, the percent conversion, yield and selectivity are presumed to be higher than the values provided in the table.

The invention claimed is:

1. A process for preparing free isocyanate, the process comprising converting a formamide into a corresponding free isocyanate by catalytic dehydrogenation, wherein:

the formamide is contacted with a catalyst and heated to a temperature of 160-240° C., the process is a homogenous catalytic process, the free isocyanate is a monoisocyanate, a diisocyanate, or a polyisocyanate, the conversion of the formamide to the corresponding isocyanate takes place in a solvent, and the catalyst is a transition metal complex of the formula:

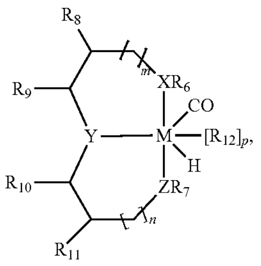

wherein:

M is Ru;

each X, Y and Z are independently P, N, or C;

each $R_6$ and $R_7$ are independently -$Ph_2$, -$(iPr)_2$, -$(tBu)_2$ or -$Et_2$;

each $R_8$ and $R_9$ are independently H, a C1-C10 alkyl, or a C5-C10 aryl;

each $R_{10}$ and $R_{11}$ are independently H, a C1-C10 alkyl, or a C5-C10 aryl;

each m and n are independently an integer of 0-3;

p is 0 or 1; and when p is 1, $R_{12}$ is Cl;

wherein optionally:

the carbon attached to $R_8$ forms a double bond with the carbon attached to $R_9$; and/or the carbon attached to $R_{10}$ forms a double bond with the carbon attached to $R_{11}$; and/or two or more of $R_8$, $R_9$, $R_{10}$, and $R_{11}$ form a ring system; and/or the carbon attached to $R_9$ forms a double bond with Y; and/or the carbon attached to $R_{10}$ forms a double bond with Y.

2. The process according to claim 1, wherein the formamide is a secondary amide.

3. The process according to claim 1, wherein the free isocyanate is a monoisocyanate of the formula:

$$R_1-(CH_2)_w-NCO,$$

wherein:

$R_1$ is a C1-C4 linear or branched alkyl, or a C5-C10 aryl; and w is an integer of 0-3.

4. The process according to claim 1, wherein the free isocyanate is a diisocyanate.

5. The process according to claim 4, wherein the free isocyanate is a diisocyanate of the formula:

$$OCN-(R_2)_x-(R_4)_a-(CH_2)_z-(R_5)_b-(R_3)_y-NCO,$$

wherein:

each $R_2$ and $R_3$ are independently $-CH_2-$, $-CH(CH_3)-$ or $-C(CH_3)_2-$;

each x and y are independently an integer of 0-5;

each $R_4$ and $R_5$ are independently a C3-C8 cyclic alkylene or C5-C10 arylene, each optionally substituted with one or more $-CH_3$ groups;

each a and b are independently an integer of 0 or 1;

and z is an integer of 0-2.

6. The process according to claim 5, wherein the diisocyanate is H12MDI, HDI, IPDI, 4,4'-MDI, 2,4'-MDI, 2,2'-MDI, m-XDI, p-XDI, m-TMXDI, p-TMXDI, NDI, 2,4-TDI or 2,6-TDI.

7. The process according to claim 1, wherein the formamide is heated to a temperature of 170-240° C.

8. The process according to claim 1, wherein the solvent is an aprotic solvent.

9. The process according to claim 8, wherein the aprotic solvent is an aromatic hydrocarbon or an ether.

10. The process according to claim 1, wherein the process takes place under inert atmosphere.

11. The process according to claim 1, wherein the conversion of the formamide to the corresponding free isocyanate takes place in the presence of an additive.

12. The process according to claim 11, wherein the additive is a base, an acid, or a hydrogen scavenger.

13. The process according to claim 11, wherein the additive is DBU, DBN, DABCO, or an alkylamine.

14. The process according to claim 11, wherein the additive is p-TsOH.

15. The process according to claim 11, wherein the additive is an olefin.

16. The process according to claim 1, wherein the transition metal complex is

I

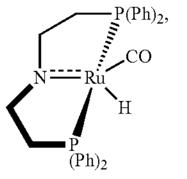

II

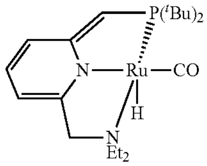

or

III

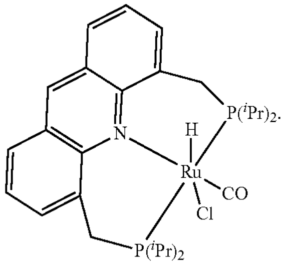

17. The process according to claim 9, wherein the aprotic solvent is toluene, dioxane or cyclopentyl methyl ether.

18. The process according to claim 15, wherein the additive is 3,3-dimethylbutene.

19. The process according to claim 1, wherein two or more of $R_8$, $R_9$, $R_{10}$, and $R_{11}$ form an aromatic C3-C6 monocyclic ring system.

20. The process according to claim 1, two or more of $R_8$, $R_9$, $R_{10}$, and $R_{11}$ form an aromatic C9-14 tricyclic ring system.

* * * * *